(12) United States Patent
Bayer et al.

(10) Patent No.: US 9,962,210 B2
(45) Date of Patent: May 8, 2018

(54) RESORBABLE METAL SCREW WITH INCREASED TORSIONAL STRENGTH FOR OSTEOPATHY

(71) Applicant: BIOTRONIK AG, Buelach (CH)

(72) Inventors: Ullrich Bayer, Bad Doberan (DE); Okechukwu Anopuo, Rostock (DE); Daniel Lootz, Rostock (DE)

(73) Assignee: BIOTRONIK AG (CH)

( * ) Notice: Subject to any disclaimer, the term of this patent is extended or adjusted under 35 U.S.C. 154(b) by 280 days.

(21) Appl. No.: 15/059,571

(22) Filed: Mar. 3, 2016

(65) Prior Publication Data

US 2016/0278834 A1   Sep. 29, 2016

Related U.S. Application Data

(60) Provisional application No. 62/137,241, filed on Mar. 24, 2015.

(51) Int. Cl.
| | |
|---|---|
| *A61B 17/86* | (2006.01) |
| *A61L 31/02* | (2006.01) |
| *A61L 31/14* | (2006.01) |
| *A61B 17/56* | (2006.01) |
| *A61B 17/16* | (2006.01) |
| *A61B 17/00* | (2006.01) |

(52) U.S. Cl.
CPC .......... *A61B 17/866* (2013.01); *A61B 17/863* (2013.01); *A61B 17/864* (2013.01); *A61B 17/8635* (2013.01); *A61L 31/022* (2013.01); *A61L 31/14* (2013.01); *A61L 31/148* (2013.01); *A61B 17/1655* (2013.01); *A61B 2017/00526* (2013.01); *A61B 2017/561* (2013.01); *A61B 2017/8655* (2013.01); *A61L 2430/02* (2013.01)

(58) Field of Classification Search
CPC .............................. A61B 17/866; A61L 31/16
See application file for complete search history.

(56) References Cited

U.S. PATENT DOCUMENTS

| 3,687,135 | A | * | 8/1972 | Stroganov | A61B 17/58 420/410 |
|---|---|---|---|---|---|
| 5,348,026 | A | | 9/1994 | Ando | |
| 2013/0304134 | A1 | * | 11/2013 | Tamai | A61L 27/047 606/301 |
| 2014/0243911 | A1 | | 8/2014 | Almarza et al. | |

FOREIGN PATENT DOCUMENTS

WO    WO 94/07425 A1    4/1994

OTHER PUBLICATIONS

European Search Report, 16158658.1—1455, Aug. 30, 2016.

* cited by examiner

*Primary Examiner* — Christian Sevilla
(74) *Attorney, Agent, or Firm* — Craig A. Fieschko, Esq.; DeWitt Ross & Stevens S.C.

(57) ABSTRACT

A bone screw formed primarily of a magnesium alloy has a self-tapping thread, and is prestressed with a retained torsional stress oriented oppositely to the direction in which the screw is screwed into bone. The pre-stressing opposes the torsional stresses arising from screwing in the screw, thereby raising the effective strength of the screw and/or allowing for a reduction in its size/mass.

20 Claims, 4 Drawing Sheets

RESORBABLE METAL SCREW WITH INCREASED TORSIONAL STRENGTH FOR OSTEOPATHY

CROSS-REFERENCE TO RELATED APPLICATIONS

This application claims priority under 35 USC § 119(e) to U.S. Provisional Patent Application 62/137,241 filed 24 Mar. 2015, the entirety of which is incorporated by reference herein.

FIELD OF THE INVENTION

The invention relates to orthopedic implants, particularly a bone screw with self-tapping thread, and to methods for producing such implants.

BACKGROUND OF THE INVENTION

Bone screws with self-tapping threads have been known for decades and constitute key fastening elements in the field of prosthetics. During their long period of use, such bone screws have been the subject of many improvements, both in terms of their materials and their geometric configuration. High-grade steel and titanium screws have enjoyed the most widespread use in the past. However, efforts are continually being made to provide orthopedic implants of different materials with comparable performance characteristics. In this regard, bone screws made of Mg (magnesium) alloys are known (see, e.g., US 2011/0313527 A1), and also screws based on magnesium with special coatings (see, e.g., US 2012/0150295 A1).

Magnesium has lower strength than titanium and high-grade steel. This makes the use of magnesium problematic for self-tapping resorbable bone screws that have to be introduced into bone tissue with high torque. Particularly in the case of small-scale and/or cannulated screws, there is the risk that the torque to be applied will exceed the torsional strength of the material, and that the screw will thus be over-tightened and will break.

SUMMARY OF THE INVENTION

The invention seeks to provide a bone screw or similar orthopedic implant with reduced failure risk and the possibility of further miniaturization, as well as a method for producing implants of this type.

The invention contemplates the forces/stresses exerted on a screw when torque is applied to screw it into bone. Since an internal torsional stress results from the torque externally exerted on the screw, with the direction of the torsional stress being determined by the direction in which the screw is screwed in (normally clockwise), the invention incorporates the concept of pre-stressing the screw with torsional stress oriented opposite the screw-in direction. This opposing stress can be impressed in the bone screw during the production process.

The effective lower torsional loading of the screw allows its cross-section, and therefore its mass, to be reduced. This considerably reduces the screw's time for degradation within, and resorption into, the body, and where the screw is made of a magnesium alloy, it also reduces the amount of hydrogen released during degradation (hydrogen release during degradation being a known problem of magnesium implants). The screw therefore provides greater biocompatibility and reduced patient rehabilitation time. Since screw size/mass can be reduced, the invention potentially offers new fields of use. e.g., in the skull and small limb field.

In an exemplary version, the bone screw has a hollow/cannulated main body with an outer diameter of 1.5-5 mm, between 2.5-3.5 mm being preferred, and an inner diameter in the range between 0.5-2.5 mm, between 0.8-1.3 mm being preferred. The reduction of the quantity of magnesium provided by the cannulation promotes reduced degradation time, and reduced hydrogen release during degradation. Reduction of hydrogen release reduces the risk of pocket-like deposition of hydrogen, where the hydrogen cannot be resorbed quickly enough by the body.

The screw thread preferably has a fine knife-like profile. Other thread profiles/cross sections are possible, such as threads with curved flanks, though such configurations may not be preferable owing to greater production complexity.

The surface of the screw can also be treated to reduce friction as it is screwed into bone, as by functionalizing the surface of the self-tapping threads. This friction reduction further decreases the torque needed to screw in the screw, and further reduces the risk of screw fracture.

The pre-stressing and surface functionalization allow multi-parameter optimization of the bone screw to meet desired application requirements, including cost. For example, if surface functionalization can be performed without cost concerns in conjunction with pre-stressing, the mass of the screw might be reduced to the greatest possible extent (or instead, the screw might be pre-stressed to a lesser extent). If surface functionalization is too costly, a designer can focus on pre-stressing the screw and/or providing it with sufficient wall thickness.

As noted above, friction can be reduced when screwing in the screw by functionalizing at least a portion of the screw surface, e.g., the thread profile of the screw. The necessary torque or torsional moment is thus decreased, and the risk of screw fracture is considerably reduced. Preferred versions of the invention further involve a surface-functionalized, self-tapping and self-lubricating thread profile wherein bioactive substances accelerating bone growth/healing, such as bone morphogenetic proteins (which promote proliferation of human bone cells), are released during and immediately after the tapping process. The thread thus has a multi-functional surface. The invention may also or instead utilize a localized additive, preferably in the form of micro-abrasives in the bioactive surface coating, to increase the self-tapping effect.

The screw is preferably formed of magnesium (Mg) or other biodegradable compounds, with the screw's surface roughness being increased by adhered and/or embedded micro-abrasives which enhance the surface's ability to cut/penetrate bone. Additionally or alternatively, polymeric hollow spheres or other microcapsules are preferably embedded in or adhered to the surface, with the microcapsules containing bioactive materials (e.g., substances promoting bone growth, preferably in liquid or pasty form) to assist with the screw's integration and absorption into the body, and/or lubricant to assist with further reducing the torque/force needed for installation of the screw. The micro-abrasives and/or microcapsules are preferably applied to the screw by forming a coating base on at least a portion of the screw (e.g., on the surface of the thread), and then applying/introducing the micro-abrasives and/or the microcapsules on/into the coating base.

When the screw is tapped/screwed into cancellous bone, local frictional moment is produced at the thread crests and the thread flanks. This results in fragmentation of the adhered and/or embedded abrasives (which are preferably hard and brittle), and also generates localized frictional temperature increases. Both effects assist with rupture of the microcapsules, resulting in release of the bioactive ingredients and/or lubricant. Due to the improved tapping effect provided by the abrasives and/or lubricant, the resistance to screwing in the screw is reduced, complementing the advantageous effects of the impressed torsional pre-stress.

In some versions of the screw, the micro-abrasives of the surface coating can be destroyed, in particular can be converted into smaller particles, by pressure and frictional heat as the screw is screwed into bone, whereby the particles effectively enlarge the screw's surface area. This increases the effective tapping ability of the screw with respect to the bone tissue. This in turn allows a possible reduction of screw dimensions, with the aforementioned advantages. The smaller particles forming from the larger abrasives additionally allow the screw to grow more quickly into the bone matrix.

The micro-abrasives may include crystalline hydroxyapatite, preferably formed as needle-shaped particles. The typical commercially-available form of this material is particularly suitable, particularly if the abrasive particles in the surface coating are oriented to increase the tapping ability and edge-holding ability of the proposed bone screw.

A preferred approach is to impress the torsional pre-stress in the still unfinished bone screw, that is, to pre-stress the bone screw while it is semi-finished. For example, a screw blank formed of a magnesium alloy can be provided, and self-tapping threads can be formed in the outer surface of the blank so as to produce the bone screw (which may define a portion of a larger orthopedic implant). The impressing of the inherent (i.e., retained) torsional stress, which is directed oppositely to the screw-in direction of the thread, can be done prior to forming the threads on the blank, or can be done while forming at least preliminary contours of the threading into the blank (e.g., when guiding the blank into a thread-cutting die in a rotary manner).

In a particularly preferred approach, the screw blank is provided as a tube or as a body including a tube portion, wherein the screw blank is pre-stressed as the self-tapping thread is formed therein during a rotary extrusion process, optionally with subsequent thread refinement via milling, grinding, cutting, or other machining. This approach tends to maximize the finished screw's retention of the pre-stressing, in contrast to an approach wherein a blank is pre-stressed and the thread is then later formed in the blank (in which case the thread formation can mechanically influence the pre-stressing). It is preferable if the milling, grinding, cutting, or other machining used to refine the threads has material removal of less than 0.2 mm, and more preferably less than 0.1 mm.

When the screw is formed via rotary extrusion, the rotary extrusion is preferably performed as hot working with a forming temperature between 100° C. and 450° C., and/or with a 0.2 to 2 revolutions per cm of screw length (assuming an outer diameter between 2.0 and 3.5 mm). Bone screws with other outer diameters may utilize a different number of revolutions per cm of screw length. Formation of the screw with a strain rate between 0.05 $s^{-1}$ and 25 $s^{-1}$, in particular between 0.07 $s^{-1}$ and 22 $s^{-1}$, is also currently preferred.

DETAILED DESCRIPTION OF EXEMPLARY VERSIONS OF THE INVENTION

Figure 1A:
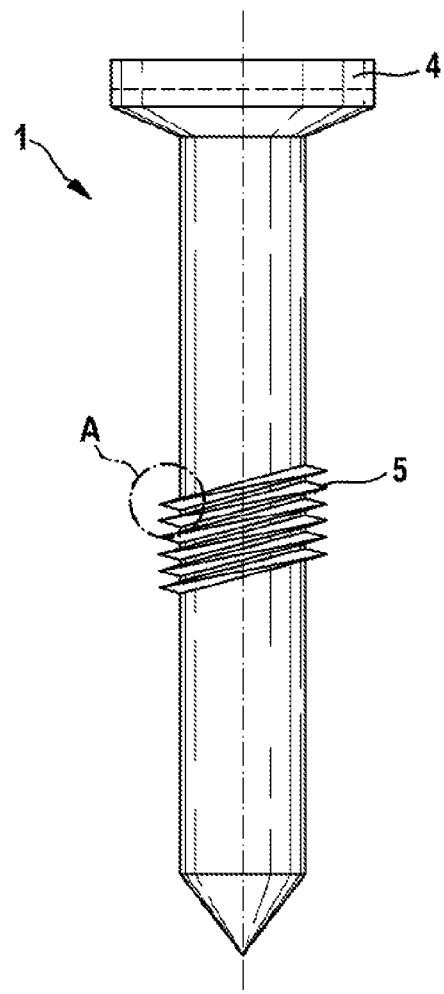
FIGS. 1A and 1B illustrate an exemplary bone screw according to the invention.
Figure 1B:
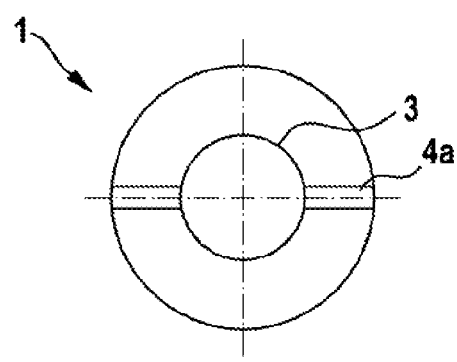

FIG. 1A shows a side view of a bone screw 1 made of an Mg alloy, which is cannulated (internally hollow). More specifically, referring to the plan view of the screw head in FIG. 1B, the bone screw 1 has a cylindrical internal passage 3, and terminates in a screw head 4 bearing a slot 4a.

Figure 2:
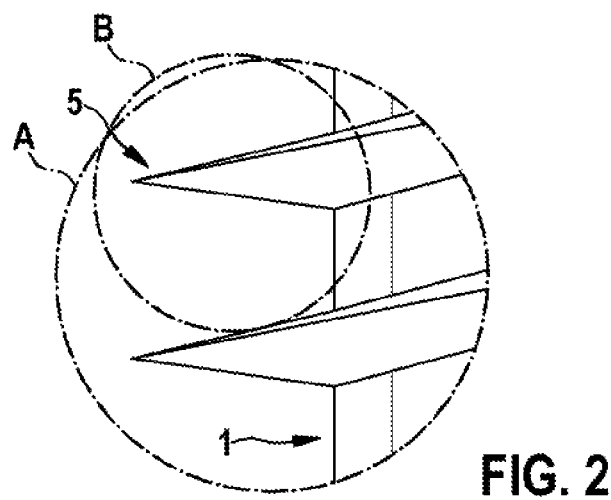
FIG. 2 shows a detailed view from FIG. 1A.

FIG. 2 shows the detail A from FIG. 1A, illustrating the screw thread 5 of the bone screw 1 in greater detail. The thread profile is a very "sharp" one with an acute angle between the flanks of the thread, with the illustrated version having an angle between the thread flanks of approximately 20°. Other angles are possible, with angles of 15°-30° being preferred depending on the specific material and purpose of the screw.

Figure 3A:
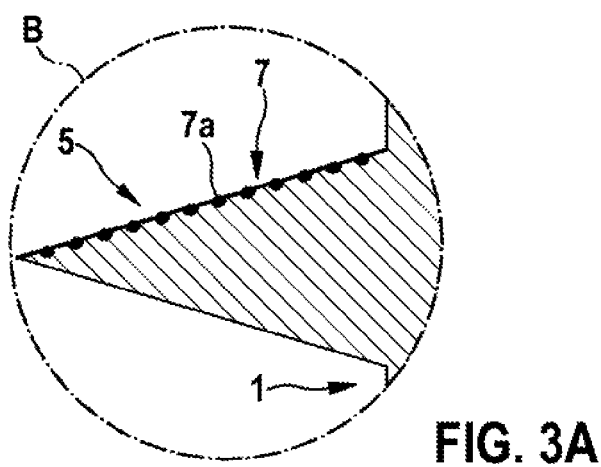
FIGS. 3A and 3B show detailed views, adapted from FIG. 2, of versions of the invention.
Figure 3B:
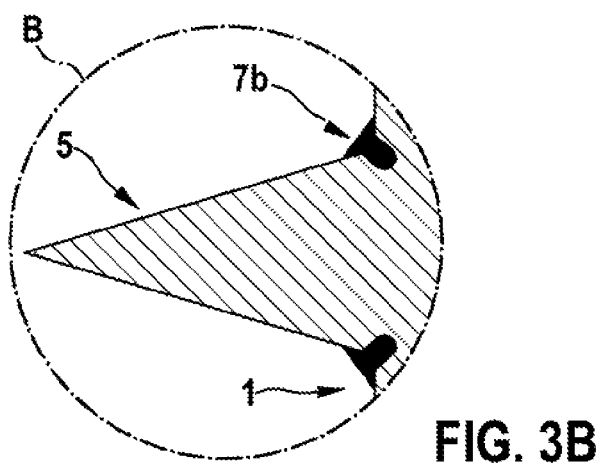

FIG. 3A shows the detail B from FIG. 2 in a sectional view, illustrating a surface coating 7 with deposited micro-abrasives 7a "anchored" in cavities of the thread flank of the screw thread 5. The further detailed view of FIG. 3B shows an alternative or additional arrangement, with the surface coating 7 of FIG. 3A omitted, wherein micro-reservoirs (microcapsules) 7b are situated where the thread flanks meet the thread roots. These microcapsules 7b are formed of a biodegradable polymer shell filled with a lubricant (which assists with bone penetration by the screw thread 5), and may also contain a medical active ingredient (e.g., for osteosynthesis) where appropriate. The microcapsules 7b of FIG. 3B can be combined with the micro-abrasives 7a shown in FIG. 3A, or either of the micro-abrasives 7a and microcapsules 7b can be used individually.

The thin surface coating 7 is preferably a biodegradable polymer which acts as a host matrix for the micro-abrasives 7a, which can be formed from hydroxyapatite (bone mineral). The microcapsules 7b can be deposited along with the surface coating 7 to adhere to the thread surface in an integrally bonded and form-fitting manner, or they can otherwise be attached to the surface of the thread 5 (preferably within cavities in the thread surface, and preferably being covered with microcrystalline hydroxyapatite after their placement). When the surface coating 7 is applied with both the micro-abrasives 7a and the microcapsules 7b, a surface composite results with hard hydroxyapatite crystals and microcapsules deposited therebetween. The micro-abrasives 7a assist with cutting and penetrating bone, and the microcapsules 7b assist with lubrication and reduction in the applied torque needed for penetration.

During the tapping process, the microcapsules 7b are destroyed mechanically, and also by thermal effects (microfrictional heat) by the fragmentation of the hard and brittle hydroxyapatite bodies (where present). The released lubricant, which can merely be a viscous carrier liquid loaded with active ingredient, results in a self-lubricating effect which further reduces the torque needed to screw in the screw. Due to the reduction of the screw-in torque, the screw experiences lower torsional loading. This allows reduction in the wall thickness of the cannulated screw, and thus in the mass of the screw (typically by 20% to 50%). The invention therefore allows further miniaturization of bone screws without increased risk of screw breakage owing to the torsional load. Further miniaturization also shortens the screw's degradation period, and reduces the quantity of hydrogen released by the screw as it degrades.

Hydroxyapatites belong to the group of calcium phosphates, which (as bone replacement materials) do not cause any endogenous defensive reactions. Hydroxyapatites, however, are brittle. This is expressed by low fracture toughness characteristic values ($K_{IC}$=1 MPam$^{1/2}$). For this reason hydroxyapatites are generally not used for load-bearing orthopedic implants, as they are susceptible to crack formation and lack mechanical durability.

Where the invention utilizes hydroxyapatites, it utilizes this alleged disadvantage rather selectively. The hydroxyapatite crystals (with a particle size range of, for example, 1-5 µm) deposited on and/or in the magnesium matrix of the screw are exposed to complex mechanical loads—tensile, compressive, and torsional stresses—during the screw-in process. These complex stresses exceed the strength of the hydroxyapatite crystals, thus resulting in their fragmentation. Microcrystalline particles (for example, 0.1-1 µm in diameter) with much greater actual surfaces are produced, with some remaining anchored in the magnesium surface of the screw, and others being shed from the surface and into the surrounding cancellous bone (with assistance from the liquid contained in the microcapsules, where present).

Figure 4A:
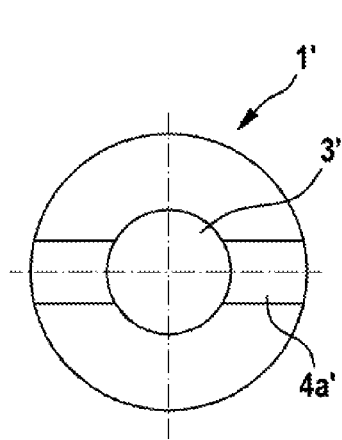
FIGS. 4A to 4B respectively show plan view and side views of a semi-finished product for producing a bone screw according to the invention.
Figure 4B:
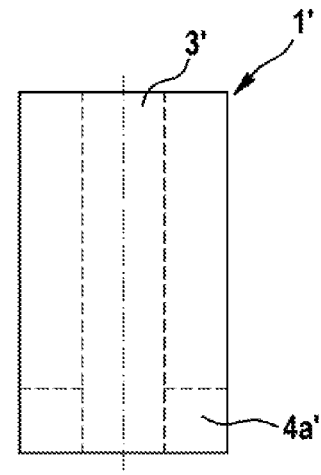

FIGS. 4A and 4B schematically illustrate the blank 1' of an exemplary bone screw according to the invention, which has an axially continuous cannula (internal passage) 3', and at an end face has a transversely-extending slot 4a'. This blank 1' is pre-stressed with an inherent torsional stress as a result of a subsequent rotary extrusion process discussed below. The slot 4a is used as an engagement point for the driver and enables the rotary extrusion.

Figure 5A:
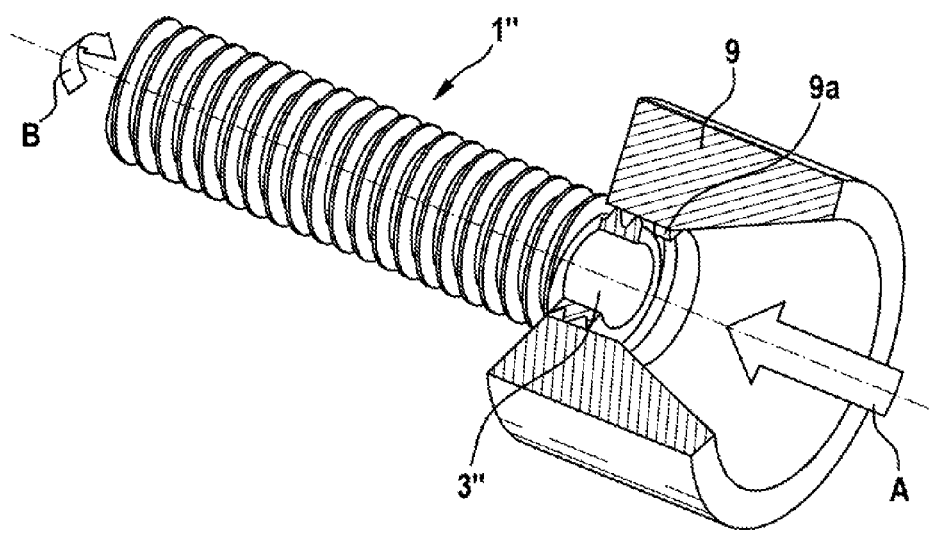
FIGS. 5A to 5C show illustrate an exemplary forming process for producing a bone screw according to the invention.
Figure 5B:
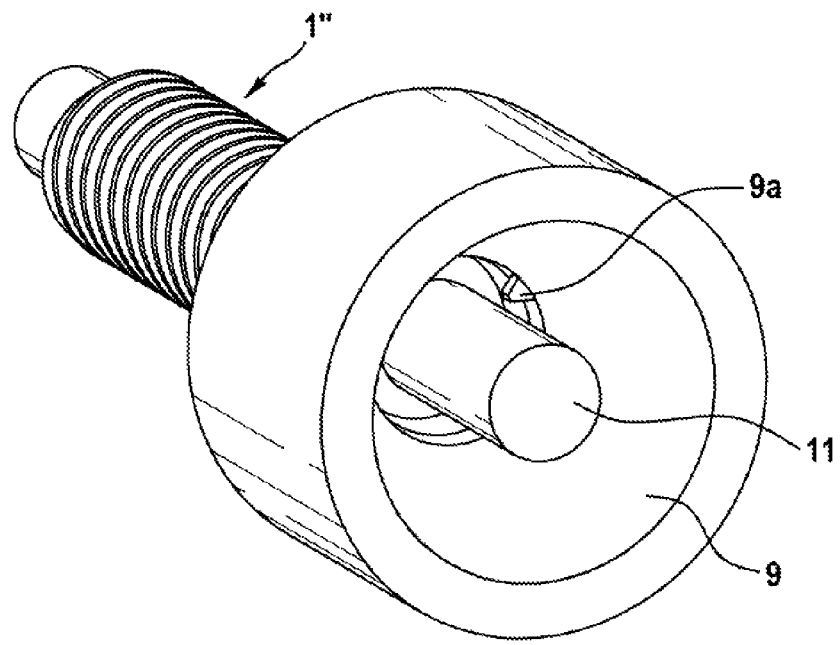
Figure 5C:
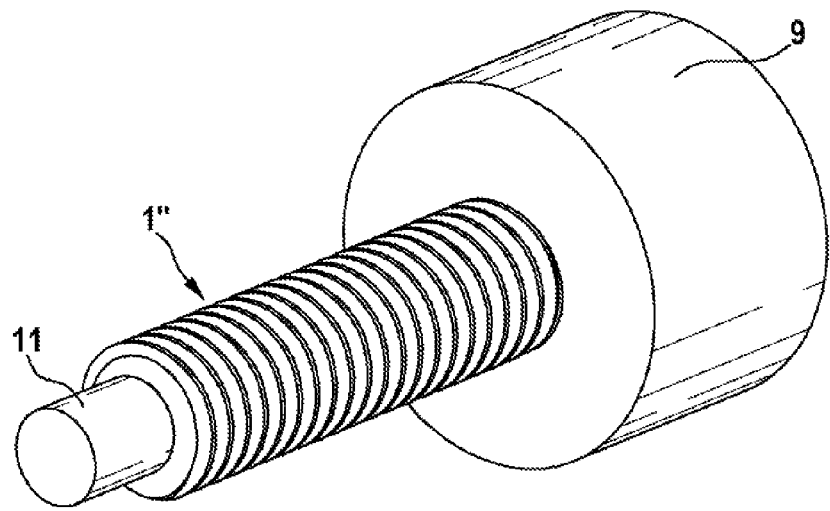

FIG. 5A to 5C show an extrusion mold/die 9 and a preliminary bone screw 1", that is, a bone screw which may be subjected to further processing to complete it for usage. The blank 1' of FIGS. 4A and 4B is guided into the extrusion mold/die 9 in a feed direction denoted by the arrow A with simultaneous rotation in a direction denoted by the arrow B, thereby forming the preliminary bone screw 1" via rotary extrusion. The reference numeral 9a in FIGS. 5A-5B denotes a shaping element/inner contour on the extrusion mold/die 9 for forming the threads on the preliminary bone screw 1". The reference numeral 11 in FIGS. 5B and 5C denotes an extrusion punch for producing the central cannula 3" of the preliminary bone screw 1" (where the central cannula 3" is not pre-formed in the blank 1'). For simplification, the driver of the extrusion punch 11, and the screw slot 4a', are not illustrated in FIGS. 5A-5C.

Details of an exemplary method for producing a bone screw according to the invention follow:
1. A blank 1' as exemplified in FIG. 4A-4B is provided. Exemplary dimensions are 12 mm length, and having a slot approximately 4 mm deep at an end face.
2. A punch having a cylindrically stepped shape is provided, with exemplary dimensions being 1.64 mm diameter for the narrower step and 4.00 mm diameter for the wider step. A "driver" protruding from the wider step is configured to engage with the slot 4a' (FIGS. 4A-4B) when the narrower step fully enters the cannula 3' of the blank 1'.
3. The narrower step is inserted within the cannula 3' of the blank 1' until the driver engages with the slot 4a'. During the extrusion, the blank 1' is introduced in a rotary manner into the extrusion mold/die 9, which has a spiraled inner structure (similarly to the negative form of a worm gear). The direction of rotation is that of the thread to be formed in/on the blank 1', and is directed opposite the thread load.
4. The forming process is continued, with rotation at constant angular velocity, until a preliminary bone screw 1" of desired length is provided.
5. When hot working a blank 1' having a rod/tube outer diameter between 2.0 and 3.5 mm, the number of revolutions is preferably between 1.0 and 8 per each centimeter of the blank 1'. The forming temperature is between 100° C. and 450° C. depending on the alloy. The strain rates during the forming process are between 0.07 s$^{-1}$ and 22 s$^{-1}$.
6. Following the forming process, which pre-stresses the screw with inherent torsional stress, the outer surface is then ground "sharp" with low material removal, thus producing the final self-tapping thread of the bone screw. Alternatively, a threading die can be used to produce a final self-tapping fine-thread profile on the bone screw.

The biodegradable Mg alloys WE43, MgCa0.8, or Az31 are exemplary materials that can be used for the blank 1'. Exemplary cross-sectional dimensions of the final bone screw are 1.0 mm wall thickness with a thread depth from 0.5 to 0.7 mm. However, the outer and inner diameter of the blank 1' (and thus the resultant wall thickness of the screw) can be varied, as can thread depth and pitch and other parameters of the screw configuration.

Rather than using an internally cannulated blank 1', a solid rod can be formed into the preliminary bone screw 1", with an outer contour substantially as described above, and pre-stressed with an inherent torsional stress. For example, solid bone screws with a length between 15 mm and 40 mm and a diameter between 2 mm and 3.5 mm can be produced.

An exemplary post-treatment method for functionalizing the screw surface is as follows:
1. The screw is cleaned in isopropanol (residence time 2 min).
2. The screw is immersed (dip coating) in a liquid formed of polylactic acid (PLA) or PLA blend containing hydroxyapatite particles (particle size between 1 and 10 Gpm), at 150° C. or more.
3. The screw is dried in a convection oven at temperatures between 60 and 80° C.
4. The coated screw is briefly immersed (<10 s) in chloroform. As a result, part of the surface is etched, leaving microcavities
5. The screw is then removed and immersed (10-30 s) in an aqueous liquid containing microcapsules. These microcapsules, having a diameter between 1 and 10 µm, have a shell made of a PLA or PLA blend which encapsulates bone morphogenetic proteins.
6. The screw is removed and dried in a convection oven at temperatures between 30 and 40° C. Some of the microcapsules will embed in the microcavities of the surface containing PLA/hydroxyapatite, and/or will adhere fixedly to the screw surface.

The versions of the invention described above are merely exemplary, and the invention is not limited to these versions. Rather, the scope of rights to the invention is limited only by the claims set out below, and the invention encompasses all different versions that fall literally or equivalently within the scope of these claims.

What is claimed is:
1. A bone screw:
   a. formed primarily of a magnesium alloy,
   b. having a screw length wherein at least a portion of the screw length bears a self-tapping thread, and c. being pre-stressed with an inherent torsional stress oriented opposite the screw-in direction of the thread.

2. The bone screw of claim 1 wherein the inherent torsional stress is constant over at least the portion of the screw length bearing the self-tapping thread.

3. The bone screw of claim 1 wherein the bone screw is cannulated along at least a portion of the screw length.

4. The bone screw of claim 3 wherein the bone screw has:
   a. an outer diameter in the range between 1.5 and 5 mm, and
   b. an inner diameter in the range between 0.5 and 2.5 mm.

5. The bone screw of claim 3 wherein the bone screw has:
   a. an outer diameter in the range between 2.5 and 3.5 mm, and
   b. an inner diameter in the range between 0.8 and 1.3 mm.

6. The bone screw of claim 1 further including a surface coating on at least a portion of the thread, wherein the surface coating includes one or more of:
   a. micro-abrasives, and
   b. microcapsules containing at least one of:
      (1) a lubricant, and
      (2) a bioactive substance configured to promote bone growth,
   wherein the microcapsules are configured to rupture as the thread penetrates bone.

7. The bone screw of claim 6 wherein the micro-abrasives include crystalline hydroxyapatite.

8. The bone screw of claim 6 wherein the micro-abrasives are needle-shaped.

9. A method for producing the bone screw of claim 1, the method including the steps of:
   a. providing a member formed primarily of a magnesium alloy;
   b. forming a self-tapping thread in an outer wall of the member, whereby the threaded member defines the bone screw;
   c. pre-stressing the member with an inherent torsional stress oriented opposite the screw-in direction of the thread.

10. The method of claim 9 wherein the step of pre-stressing the member occurs at least partially simultaneously with the step of forming the self-tapping thread.

11. The method of claim 9 wherein the step of forming the self-tapping thread includes urging the member through a die while rotating at least one of the member and the die.

12. The method of claim 11 wherein the step of forming the self-tapping thread further includes cutting and/or grinding the member.

13. The method of claim 12 wherein cutting and/or grinding the member removes less than 0.2 mm from the diameter of the member.

14. The method of claim 11 wherein the step of forming the self-tapping thread occurs at a temperature above 100° C.

15. The method of claim 11 wherein the step of forming the self-tapping thread occurs at a strain rate between 0.05 $s^{-1}$ and 25 $s^{-1}$.

16. The method of claim 11 wherein the step of forming the self-tapping thread includes rotating the member with respect to the die by 1.0 to 8 revolutions per centimeter of advancement of the member through the die.

17. The method of claim 9 wherein the member is at least partially defined by a tube.

18. The method of claim 9 further including the steps of:
   a. forming a surface coating on at least a portion of the thread; and
   b. providing one or more of:
      a. micro-abrasives, and
      b. microcapsules containing at least one of:
         (1) a lubricant, and
         (2) a bioactive substance configured to promote bone growth, to the surface coating.

19. The method of claim 18 wherein the micro-abrasives and/or the microcapsules are provided to the surface coating prior to forming the surface coating on at least a portion of the thread.

20. A method for producing the bone screw of claim 1, the method including the steps of:
   a. providing a member formed primarily of a magnesium alloy;
   b. forming a self-tapping thread in the member via rotary extrusion, whereby the threaded member defines the bone screw.

* * * * *